US012109105B2

(12) United States Patent
D'Agostino et al.

(10) Patent No.: US 12,109,105 B2
(45) Date of Patent: Oct. 8, 2024

(54) SYSTEMS AND METHODS FOR ATTACHING SOFT TISSUE TO AN IMPLANT

(71) Applicant: Onkos Surgical, Inc., Parsippany, NJ (US)

(72) Inventors: John D'Agostino, West New York, NJ (US); Daniel Haberman, Hoboken, NJ (US); Felasfa M. Wodajo, Fairfax, VA (US)

(73) Assignee: ONKOS Surgical, Inc., Parsippany, NJ (US)

( * ) Notice: Subject to any disclaimer, the term of this patent is extended or adjusted under 35 U.S.C. 154(b) by 0 days.

(21) Appl. No.: 18/236,615

(22) Filed: Aug. 22, 2023

(65) Prior Publication Data
US 2023/0397982 A1    Dec. 14, 2023

Related U.S. Application Data

(63) Continuation of application No. 17/222,172, filed on Apr. 5, 2021, now Pat. No. 11,737,861, which is a
(Continued)

(51) Int. Cl.
| A61F 2/30 | (2006.01) |
| A61B 17/04 | (2006.01) |
| A61F 2/08 | (2006.01) |
| A61F 2/38 | (2006.01) |
| A61F 2/34 | (2006.01) |

(52) U.S. Cl.
CPC ........ *A61F 2/0811* (2013.01); *A61B 17/0401* (2013.01); *A61F 2/30* (2013.01); *A61F 2/3859* (2013.01); *A61B 2017/0414* (2013.01); *A61F 2002/0852* (2013.01);
(Continued)

(58) Field of Classification Search
CPC .......... A61F 2/0811; A61F 2/3859; A61F 2002/0852; A61F 2002/348; A61F 2/30749; A61F 2/30907; A61B 17/0401
See application file for complete search history.

(56) References Cited

U.S. PATENT DOCUMENTS

| 4,728,335 A | 3/1988 | Jurgutis et al. |
| 1,863,474 A | 9/1989 | Brown et al. |

(Continued)

FOREIGN PATENT DOCUMENTS

CN    105193527 A    12/2015

OTHER PUBLICATIONS

International Application No. PCT/US2019/047072, International Search Report and Written Opinion mailed Jan. 9, 2020, 13 pages.
(Continued)

*Primary Examiner* — Bruce E Snow
(74) *Attorney, Agent, or Firm* — Corner Counsel, LLC (57) ABSTRACT

Methods for affixing soft tissue to an implant. The implant has a soft tissue attachment structure that includes a surface defining one or more troughs, and either at least one ingrowth plate spanning a portion of the trough and defining a suture tunnel between the ingrowth plate and trough for receiving a suture, or fixation bridges spanning a portion of the one or more troughs, each fixation bridge and respective trough defining a suture tunnel for receiving suture. Systems for performing the method are also disclosed.

10 Claims, 9 Drawing Sheets

Related U.S. Application Data continuation of application No. 16/131,371, filed on Sep. 14, 2018, now Pat. No. 11,000,360.

(52) U.S. Cl.
CPC ............... *A61F 2002/30433* (2013.01); *A61F 2002/30914* (2013.01); *A61F 2002/348* (2013.01)

(56) References Cited

U.S. PATENT DOCUMENTS

| | | | |
|---|---|---|---|
| 4,883,492 A | 11/1989 | Frey et al. | |
| 5,209,756 A | 5/1993 | Seedhorn et al. | |
| 5,211,661 A | 5/1993 | Shinjou et al. | |
| 5,489,306 A | 2/1996 | Gorski | |
| D374,287 S | 10/1996 | Goble et al. | |
| 6,132,442 A | 10/2000 | Ferragamo et al. | |
| 6,168,596 B1 | 1/2001 | Wellisz et al. | |
| 6,245,110 B1 | 6/2001 | Grundei et al. | |
| 6,371,985 B1 | 4/2002 | Goldberg | |
| 6,383,187 B2 | 5/2002 | Tormala et al. | |
| 6,454,810 B1 | 9/2002 | Lob | |
| 6,482,232 B1 | 11/2002 | Boucher et al. | |
| 6,592,622 B1 | 7/2003 | Ferguson | |
| 6,824,566 B2 | 11/2004 | Kana et al. | |
| 6,866,666 B1 | 3/2005 | Sinnott et al. | |
| 7,001,429 B2 | 2/2006 | Ferguson | |
| 7,070,622 B1 | 7/2006 | Brown et al. | |
| 7,175,664 B1 | 2/2007 | Lakin | |
| 7,294,149 B2 | 11/2007 | Hozack et al. | |
| 8,118,868 B2 | 2/2012 | May et al. | |
| 8,177,849 B2 | 5/2012 | Meyers et al. | |
| 8,182,542 B2 | 5/2012 | Ferko | |
| 8,226,725 B2 | 7/2012 | Ferko | |
| 8,348,975 B2 | 1/2013 | Dreyfuss | |
| 8,469,999 B2 | 6/2013 | Gonzalez-Hernandez | |
| 8,608,777 B2 * | 12/2013 | Kaiser | A61B 17/06166 606/232 |
| 8,623,026 B2 | 1/2014 | Wong et al. | |
| 8,690,916 B2 | 4/2014 | Gonzales-Hernandez | |
| 8,858,634 B2 | 10/2014 | Lewallen | |
| 8,979,940 B2 | 3/2015 | Porter et al. | |
| 9,005,305 B2 | 4/2015 | Meyers et al. | |
| 9,056,012 B2 | 6/2015 | Crabtree, Jr. et al. | |
| 9,278,003 B2 | 3/2016 | Deffenbaugh et al. | |
| 9,289,299 B2 | 3/2016 | Metzger et al. | |
| 9,345,580 B2 | 5/2016 | Porter et al. | |
| 10,251,744 B2 | 4/2019 | Treacy et al. | |
| 10,675,151 B2 | 6/2020 | Yadav et al. | |
| 11,000,360 B2 | 5/2021 | D'Agostino et al. | |
| 11,737,861 B2 * | 8/2023 | D'Agostino | A61F 2/30907 623/13.14 |
| 2001/0011193 A1 | 8/2001 | Nogarin | |
| 2003/0105465 A1 | 6/2003 | Schmieding et al. | |
| 2006/0241776 A1 | 10/2006 | Brown et al. | |
| 2007/0129809 A1 | 6/2007 | Meridew et al. | |
| 2007/0203499 A1 | 8/2007 | Boucher et al. | |
| 2008/0255622 A1 | 10/2008 | Mickiewicz et al. | |
| 2010/0298947 A1 | 11/2010 | Unger | |
| 2011/0009973 A1 | 1/2011 | Meyers et al. | |
| 2011/0054625 A1 | 3/2011 | Ferko et al. | |
| 2011/0130840 A1 | 6/2011 | Oskouei | |
| 2011/0144760 A1 | 6/2011 | Wong et al. | |
| 2011/0224796 A1 | 9/2011 | Weiland et al. | |
| 2012/0035733 A1 | 2/2012 | Porter et al. | |
| 2013/0030540 A1 | 1/2013 | Leibinger | |
| 2013/0317510 A1 | 11/2013 | Couture et al. | |
| 2014/0257294 A1 | 9/2014 | Gedet et al. | |
| 2014/0288657 A1 | 9/2014 | Gobezie et al. | |
| 2016/0199071 A1 | 7/2016 | Callazo | |
| 2016/0296336 A1 | 10/2016 | Maale et al. | |
| 2017/0360453 A1 | 12/2017 | Brailovski et al. | |
| 2018/0214261 A1 | 8/2018 | Treacy et al. | |

OTHER PUBLICATIONS

Agarwal, M., et al. "Joint-sparing or Physeal-sparing Diaphyseal Resections: The Challenge of Holding Small Fragments,", Clinical Orthopaedics and Related Research, vol. 468, No. 11, Nov. 2010, pp. 2924-2932.

Stevenson, J.D., et al. "Minimising aseptic loosening in extreme bone resections," The Bone & Joint Journal, vol. 99-B, No. 12, Dec. 2017, pp. 1689-1695.

Wong, K.C., et al. "Joint-preserving Tumor Resection and Reconstruction using Image-Guided Computer Navigation," Clinical Orthopaedics and Related Research, vol. 471, No. 3, Mar. 2013, pp. 762-773.

Poster entitled "Custom Trabecular Metal Joint Sparing Endoprosthesis for Metaphyseal Reconstruction in Sarcoma: A Case Series", presented at Meeting of the National Medical Association, Jun. 2011.

GMRS Proximal Tibia Global Modular Replacement System, prior art as stated by applicant.

International Application No. PCT/US2019/047072, Invitation to Pay Additional Fees mailed Oct. 28, 2019, 2 pages.

* cited by examiner

SYSTEMS AND METHODS FOR ATTACHING SOFT TISSUE TO AN IMPLANT

RELATED APPLICATIONS

This application is a continuation of U.S. patent application Ser. No. 17/222,172, filed Apr. 5, 2021, which is a continuation of U.S. patent application Ser. No. 16/131,371, filed Sep. 14, 2018, the disclosures of both of which are incorporated herein by reference in their entireties.

BACKGROUND OF THE INVENTION

(1) Field of the Invention

The present disclosure relates generally to implants, including orthopaedic implants for joint replacement, and more particularly to features of such implants for fixation of soft tissue thereto.

(2) Description of the Prior Art

Many implants, including orthopaedic implants for joint replacement, do not have adequate soft tissue fixation features that allow for successful re-attachment of soft tissue and consequent functionality of the surrounding anatomy after implantation. Some existing limb-salvage systems including proximal tibia and proximal femur replacements have soft tissue attachment features integrated into the implant. Many of these existing systems have suture holes on either side of porous coated areas. An example system is the GMRS® (Global Modular Replacement System) Proximal Tibial Replacement sold by Stryker Orthopedics, Kalamazoo, Mich. Sutures are passed through the suture holes and through or over soft tissue in an attempt to hold the soft tissue against the porous coated areas. The goal is to try to promote ingrowth and fixation of the soft tissue to the porous coating.

SUMMARY OF THE INVENTION

In an embodiment, the present invention includes a method for affixing soft tissue to an implant, comprising the step of providing an implantable component having a soft tissue attachment structure including a surface defining a trough, and at least one ingrowth plate spanning a portion of the trough and defining a suture tunnel between the ingrowth plate and trough for receiving a suture. The method further comprises the steps of implanting the implantable component to skeletal bone such that soft tissue overlies the at least one ingrowth plate, and passing the suture through the trough, over the soft tissue overlying the at least one ingrowth plate, and back through the trough in a loop In another embodiment, the present invention includes a method for affixing soft tissue to an implant, comprising the step of providing an implantable component having a soft tissue attachment structure including a surface defining a trough, and an ingrowth plate spanning a portion of the trough and defining a suture tunnel between the ingrowth plate and trough for receiving suture, wherein the ingrowth plate bows convexly away from the surface. The method further comprises the steps of implanting the implantable component to skeletal bone such that soft tissue overlies the convex ingrowth plate, and passing suture through the trough, over the soft tissue overlying the ingrowth plate, and back through the trough in a loop.

In yet another embodiment, the present invention includes a method for affixing soft tissue to an implant, comprising the step of providing an implantable component having a soft tissue attachment structure including a surface defining a spaced pair of troughs, a first fixation bridge spanning a portion of one of the pair of troughs and a second fixation bridge spanning a portion of the other of the pair of troughs, the second fixation bridge being separated from and non-continuous with the first fixation bridge. Each fixation bridge and respective trough defines a suture tunnel for receiving suture, and the surface further defines a soft tissue ingrowth patch between the spaced pair of troughs. The method further comprises the steps of implanting the implantable component to skeletal bone such that soft tissue overlies the soft tissue ingrowth patch; and passing a suture through a first one of the spaced pair of troughs, over the soft tissue overlying the soft tissue ingrowth patch, and back through the first one of the spaced pair of troughs in a loop.

These and other objects of the present invention will be apparent from review of the following specification and the accompanying drawings.

BRIEF DESCRIPTION OF THE DRAWINGS

The accompanying drawings, which are incorporated in and constitute a part of the specification, illustrate preferred embodiments of the invention and, together with the description, serve to explain the objects, advantages, and principles of the invention.

DETAILED DESCRIPTION OF THE INVENTION

Soft tissue attachment to metal prostheses remains an unsolved issue within the implant space generally, and the orthopedic space more particularly. The present invention solves this unmet need by providing a structure and method to fixate soft tissue to a metal prosthesis using both mechanical and biologic factors. This is advantageous as it leverages soft tissue repair methods and applies such methods to include a system of attachment sites within a metal prosthesis.

Figure 1:
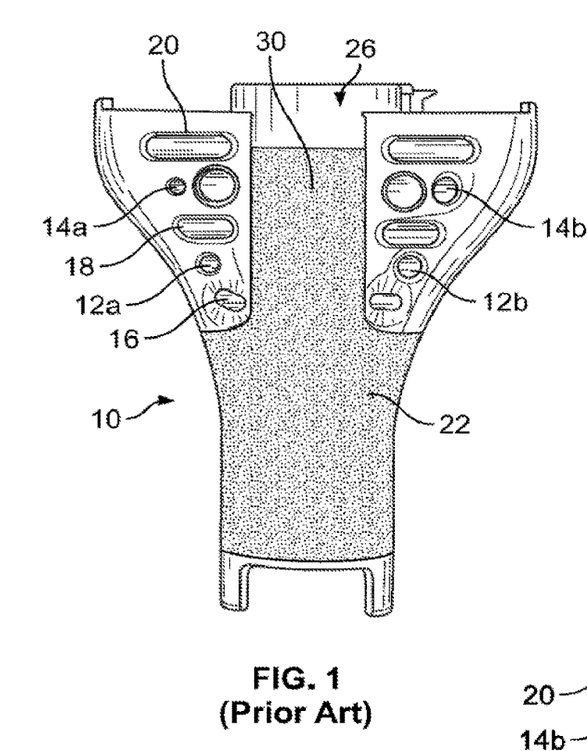
FIG. 1 is a front (anterior) view of a proximal tibial component in accordance with the prior art.
Figure 2:
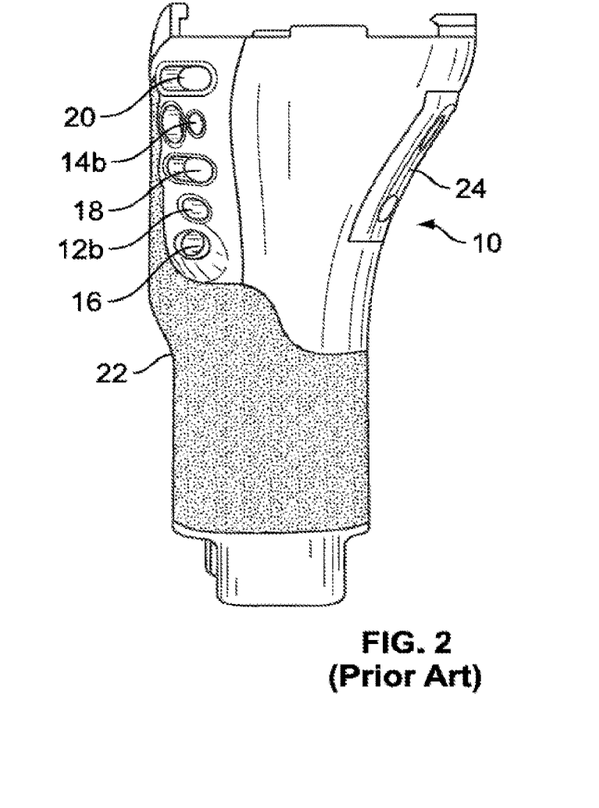
FIG. 2 is a side (lateral) view of the prior art proximal tibial component of FIG. 1.

A prior art proximal tibial component 10, as illustrated in FIGS. 1 and 2, includes a plurality of anterior-posterior oriented through holes 12a, 12b, and 14a, 14b, disposed medially and laterally of the longitudinal axis of the tibial component 10 and spaced apart along the general direction of the longitudinal axis. A plurality of medial-lateral oriented through holes 16, 18 and 20 are disposed adjacent the anterior face 22 of the tibial component 10 and are spaced apart along the general direction of the longitudinal axis of the tibial component. Through holes 12a, 12b, and 14a, 14b are open at the anterior face 22 and posterior face 24, respectively.

A bridge portion 26 of the anterior face 22 is located between holes 12a, 14a and holes 12b, 14b, respectively. Medial-lateral through holes 16, 18 and 20 form tunnels beneath bridge portion 26. Sutures may be passed through any or all of holes 12a, 12b, 14a, 14b, 16, 18 and 20 to secure soft tissue to tibial component 10. Sutures passed through any of holes 12a through 14b, or through any of the tunnels formed by holes 16, 18 and 20, can be placed to overlie or pierce soft tissue located adjacent bridge portion 26 with the object of holding the soft tissue in contact with a porous ingrowth surface 30 on the face 22 of bridge portion 26. The intended purpose of such suturing is to encourage growth of the soft tissue into the porous surface 30 for fixation to the tibial component 10.

Figures 3, 4, 5:
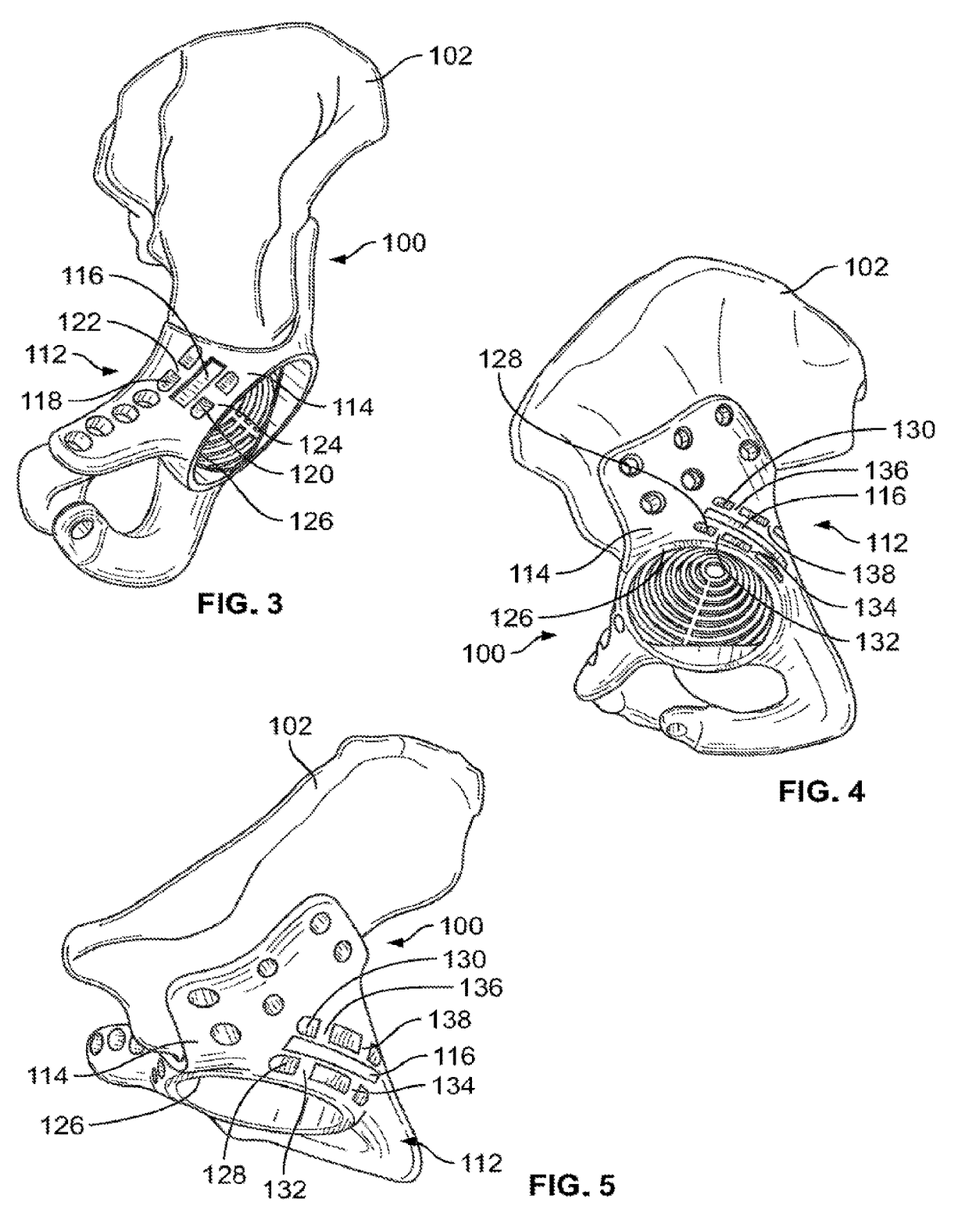
FIG. 3 is a front (anterior) view of a half pelvis having a replacement acetabular cup implanted thereon in accordance with a first embodiment of the present invention.
FIG. 4 is a rear (posterior) view of the half pelvis and replacement acetabular cup of FIG. 3.
FIG. 5 is a tilted side (lateral) view of the half pelvis and replacement acetabular cup of FIG. 3.

Referring to FIGS. 3, 4 and 5, a replacement acetabular component 100 is shown implanted to a pelvis 102 in accordance with an embodiment of the present invention. Generally, the acetabular component 100 includes a system of suture tunnels 112 set in parallel (or in a matrix array) within a metal body. Together with each system of suture tunnels 112, and between adjacent tunnels, the surface 114 of the metal acetabular component 100 has a porous three-dimensional ingrowth patch 116 with a porous structure having pore spacing that is receptive to soft tissue. The structure allows an approach to attach remaining soft tissue to metal using a suture bridge technique. This construct and technique provides at least two points of fixation, or anchors, and provides compression of soft tissue into the porous ingrowth surface 116 by bridging the suture between two anchor points and over or through the tissue.

Replacement acetabular component 100 is configured for reconstruction of the soft tissue hip capsule during a pelvic reconstruction with a large metal prosthesis. Referring to FIG. 3 in particular, there is a set of parallel suture tunnels 118 and 120, each with one fixation site 122 and 124, respectively, disposed in the anterosuperior aspect of the acetabular rim 126. Similarly (see FIGS. 4 and 5), there is a set of parallel suture tunnels 128 and 130, each with two fixation points 132,134, and 136,138, respectively, disposed in an array in the superolateral aspect of the acetabulum and towards the reconstructed ilium. This placement allows for reconstruction of the pubofemoral ligament and iliofemoral ligament according to their original attachment sites on the native pelvis, as well as any additional muscular attachments that the surgeon desires. A slot may be provided through the acetabular cup to allow for screw placement in various orientations allowing for flexibility of fixation during implantation.

In FIG. 3, suture tunnels 118 and 120 comprise spaced, generally parallel grooves or troughs depressed in the surface 114 of the acetabular component 100 and extending generally parallel to the rim 126. Fixation sites 122 and 124 each comprise a bridge that spans transversely across respective grooves 118 and 120, such that grooves 118 and 120 each form a tunnel beneath respective fixation bridges 122 and 124. Sutures can be looped through each tunnel 118, 120 under the respective bridge 122, 124 such that bridges 122,124 serve as attachment points for the suture. The width of bridges 122, 124 may be sized to correspond to commonly used surgical needles to facilitate easier passing of sutures thereunder. By passing the suture between tunnels 118 and 120, i.e., from attachment point 122 to attachment point 124 and over ingrowth surface 116, soft tissue trapped between the suture and surface 116 can be pressed into contact with porous surface 116 to promote growth thereto and fixation of the soft tissue to acetabular component 100. Additionally, multiple sutures can be accommodated under one bridge, thus enabling for more pressure to be applied to tissue, and for consequently more ingrowth of tissue.

Referring to FIGS. 4 and 5, suture tunnels 128 and 130 comprise spaced, generally parallel grooves or troughs depressed in the surface 114 of the acetabular component 100 and extending generally parallel to the rim 126. Of course, other configurations are also clearly contemplated. Fixation sites 132 and 136 each comprise a bridge that spans transversely across respective grooves 128 and 130, such that grooves 128 and 130 each form a tunnel beneath respective fixation bridges 132 and 136. Similarly, fixation sites 134 and 138 each comprise a bridge that spans transversely across respective grooves 128 and 130, such that grooves 128 and 130 each form a second tunnel beneath respective fixation bridges 134 and 138. Bridges 132 and 134 are spaced such that each provides a separate suture fixation site, respectively, with regard to groove 128. Bridges 136 and 138 are spaced such that each provides a separate suture fixation site, respectively, with regard to groove 130. Sutures can be looped through each tunnel 128, 130 under the respective bridge 132, 136. Similarly, sutures can be looped through each tunnel 128, 130 under the respective bridge 134, 138 such that bridges 134,138 serve as attachment points for the suture. By passing the suture between tunnels 128 and 136, i.e., from attachment point 132 to attachment point 136 and over ingrowth surface 116, soft tissue trapped between the suture and surface 116 can be pressed into contact with porous surface 116 to promote growth thereto and fixation of the soft tissue to acetabular component 100. Similarly, suture can be passed from attachment point 134 to attachment point 138. Alternatively, suture can be passed from anchor points 132 to 138, and from anchor points 134 to 136, in a criss-cross fashion, if desired. The number, size, orientation and spacing of the bridges across grooves 128 and 130 can be changed as desired to provide a multiplicity of suture attachment sites with corresponding multiplicity of options regarding the path of the suture between and among the attachment sites.

Figure 6:
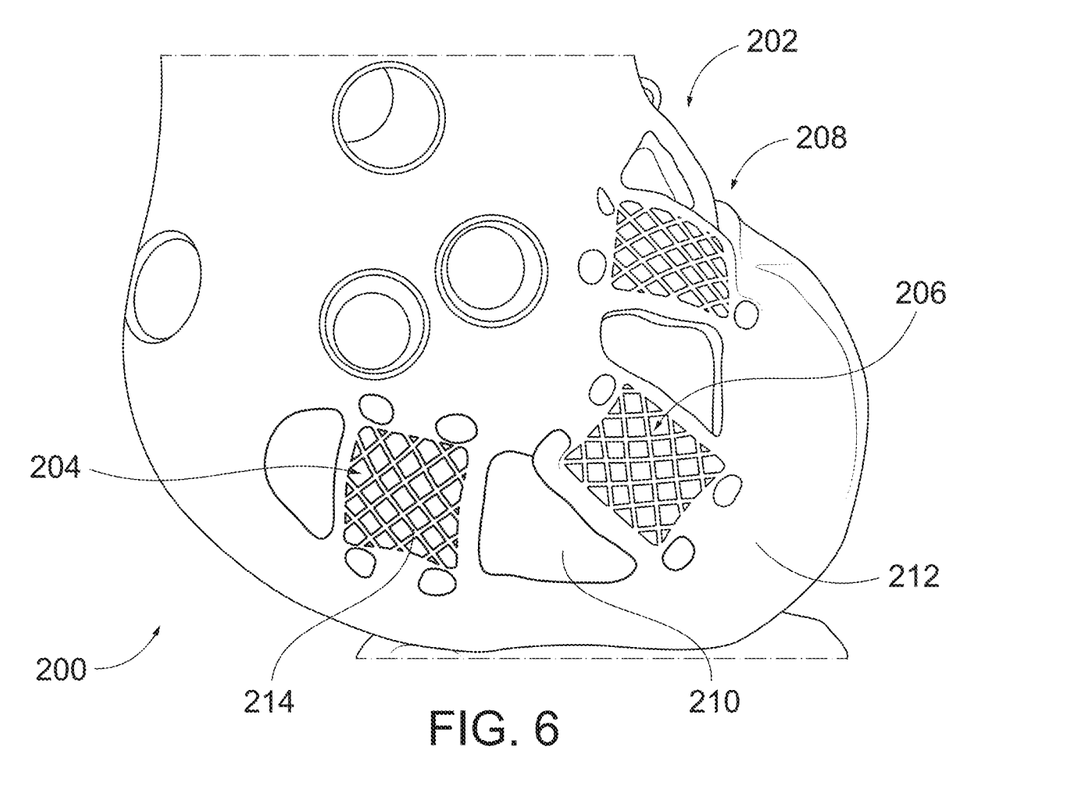
FIG. 6 is a side (lateral) view of a replacement distal femoral component in accordance with a second embodiment of the present invention.

Referring to FIG. 6, another embodiment of the invention includes a replacement femoral component 200 of an orthopedic oncology knee implant having an integrated soft tissue attachment structure 202 on the outside of a prosthetic lateral condyle. One purpose of this structure 202 is to allow for the initial approximation of tendons, ligaments and other soft tissue structures to their original anatomic location when that area of the bone is removed during surgery. The attachment structure 202 also allows for long-term ingrowth and biologic fixation of the soft tissue to the femoral component 200. In addition to providing for areas of ingrowth, structure 202 provides for adequate compression of the soft tissue thereto by suture to promote ingrowth, which is facilitated by the configuration of the attachment structure 202. Major elements of attachment structure 202 include ingrowth plates 204, 206 and 208 that each span a groove or trough 210 depressed below the outer surface 212 of the side of the condyle. In this embodiment, trough 210 runs generally parallel to the curvature of the face of the condyle in an L, C or U configuration. Trough 210 is deep enough to accommodate the size of the suture needle to be used.

Each ingrowth plate 204, 206, 208, of which ingrowth plate 204 may be regarded as representative, bows out convexly from the outer surface 212 of the implant as illustrated in FIGS. 6-10. Plate 204 has a honeycomb, mesh, or otherwise perforated plate portion 214 to encourage soft tissue growth. Plate portion 214 spans trough 210 from a first rim 216 to a second rim 218 at the opening of trough 210. At respective opposite sides of plate portion 214 and integral therewith are reinforcing rods 220 and 222 that likewise span trough 210 from first rim 216 to second rim 218. Rods 220, 222 are convexly curved along with plate portion 214 to bow outwardly from outer surface 212. A pair of depressions 224, 226 is oriented in the outer surface of rod 220 facing away from plate portion 214. Similarly, a pair of corresponding depressions 228, 230 is oriented on the outer surface of rod 222 facing away from plate portion 214 in a direction opposite the direction in which depressions 224, 226 face. The corresponding matching pairs of depressions roughly define lines that are generally parallel to the longitudinal axis of trough 210 where it is spanned by plate portion 214. Depressions 224, 226, 228 and 230 at the edges of plate 204 are configured to receive and stabilize sutures to be wrapped around the plate through the trough 210 to overlie and compress soft tissue against plate portion 214 to facilitate ingrowth and fixation. Of course, any number, shapes, sizes and quantities of depressions or other such surface configurations are also contemplated.

Extending outwardly of outer surface 212, adjacent rims 216 and 218 respectively, where plate 204 connects thereto, are a pair of elongated protrusions 232, 234 running generally parallel to rims 216, 218. Each protrusion 232, 234 defines a respective tunnel or bore 236, 238, comprising suture eyelets, running generally parallel to rims 216, 218 and open at opposite ends. The holes in the eyelets are wide enough in diameter and have a radius of curvature adequate to pass the suture needle used for attaching the suture to the implant, whereby soft tissue may be sutured to the implant. Two sutures can be passed through tissue and through each of bore 236 and 238, separately. Alternatively, a single suture can be passed through tissue and through both bores 236 and 238 in a criss-cross fashion, applying increased pressure on tissue against plate 214 to further facilitate ingrowth and fixation.

Figure 7:
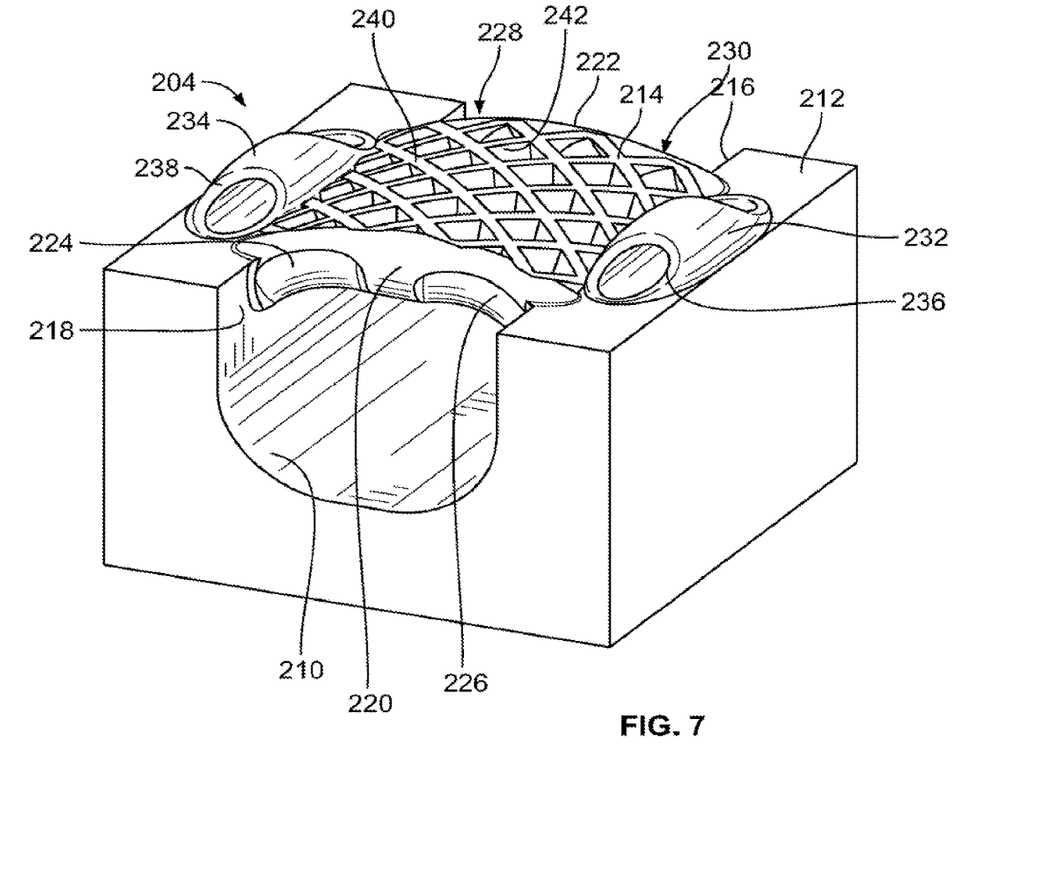
FIG. 7 is an enlarged perspective cut-away view of a soft tissue fixation portion of the replacement distal femoral component of FIG. 6.
Figure 8:
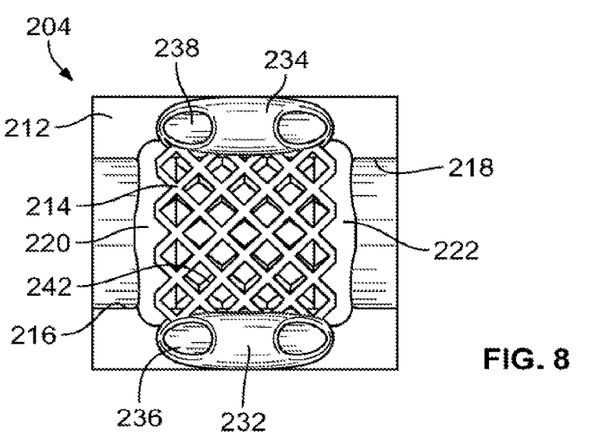
FIG. 8 is a normal view of the soft tissue fixation portion of FIG. 7.
Figure 9:
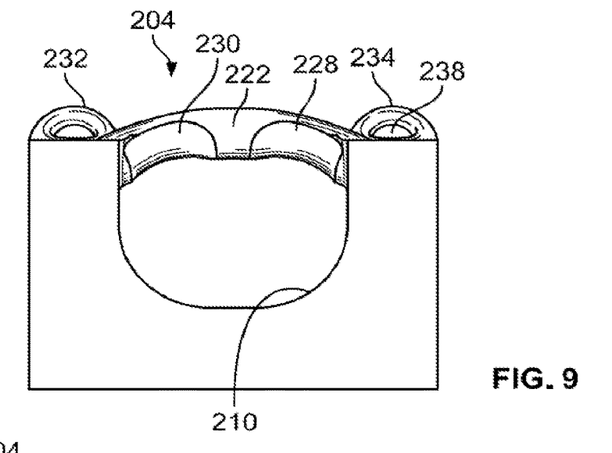
FIG. 9 is an end view of the soft tissue fixation portion of FIG. 7.
Figure 10:
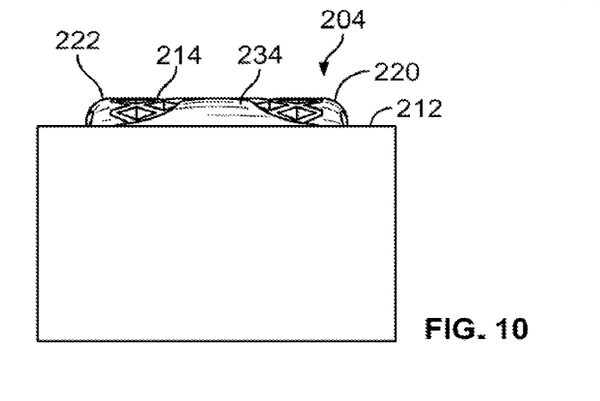
FIG. 10 is a side view of the soft tissue fixation portion of FIG. 7.

Plate portion 214 includes a plurality of intersecting rows of walls 240 arranged diagonally with respect to the direction of span of plate 204, such that some of the rows intersect others of the rows at angles to define square, rectangular or diamond-shaped holes 242 that open normally to the convex surface of plate portion 214. Holes 242 are sized and configured to accommodate and facilitate ingrowth of soft tissue for fixation to attachment structure 202 of implant 200. Sutures can be passed both through the suture eyelets and underneath the ingrowth plates.

The sizes and position of plates and suture eyelets and the number, shape and position of each hole 242 can be varied depending on the implant and the anatomy to which the implant 200 is to be affixed. Further, the lattice structure could be made of smaller holes or cells mimicking a porous lattice.

Figure 11:
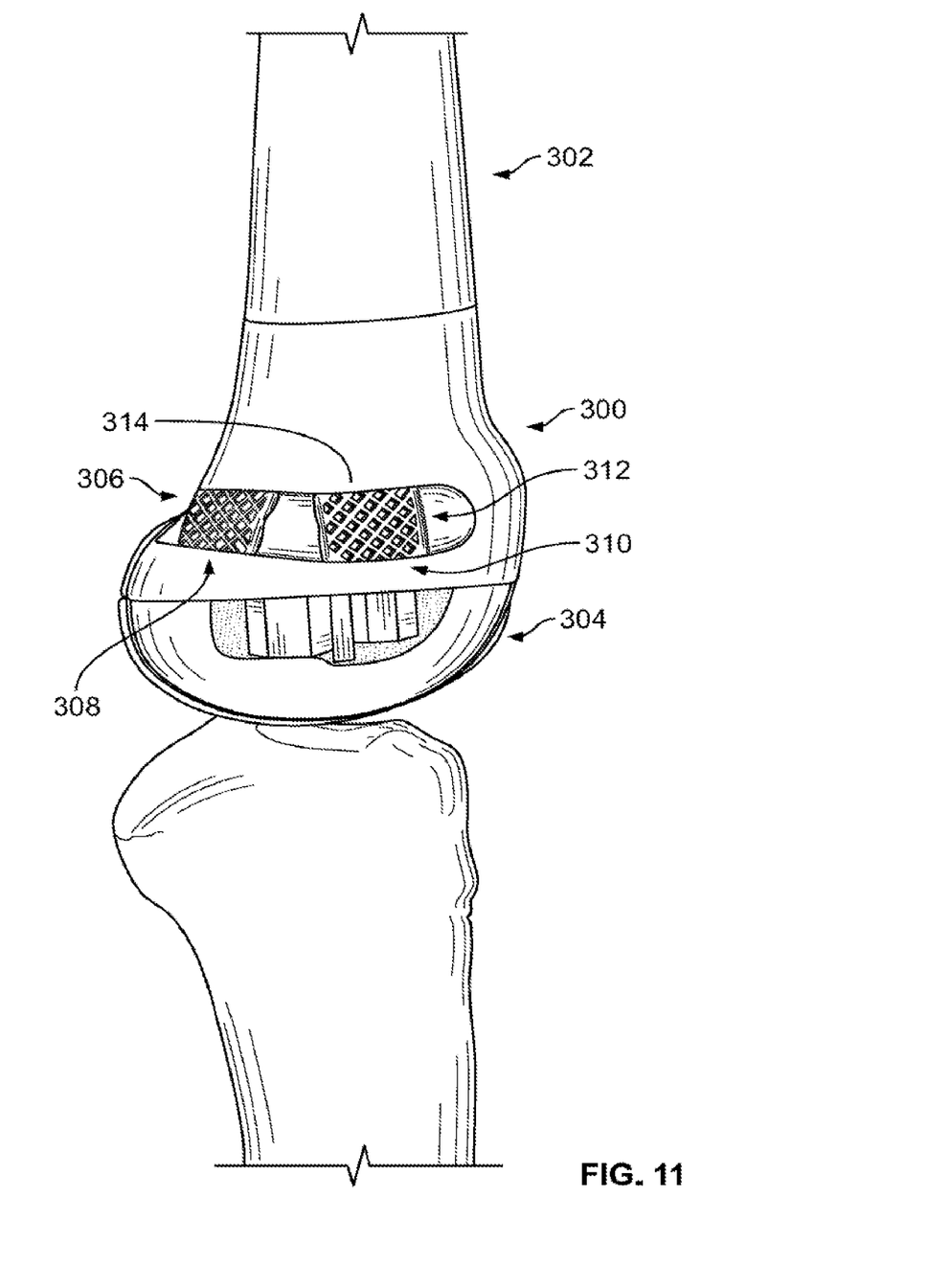
FIG. 11 is a side view of an orthopedic implant in accordance with a third embodiment of the present invention.

Referring to FIG. 11, yet another embodiment of the invention includes a femoral prosthesis component 300 for replacing a segment of metaphyseal and/or epiphyseal bone of a femur 302 when it is medically feasible to perform a resection that spares the femoral condyle surface 304 of the knee joint. Component 300 includes an integrated soft tissue attachment structure 306 on the outside of a lateral surface of the component. One purpose of this structure 306 is to allow for the initial approximation of tendons, ligaments and other soft tissue structures to their original anatomic location when that area of the bone is removed during surgery. The attachment structure 306 also allows for long-term ingrowth and biologic fixation of the soft tissue to the femoral component 300. In addition to providing for areas of ingrowth, structure 306 provides for adequate compression of the soft tissue thereto by suture to promote ingrowth, which is facilitated by the configuration of the attachment structure 306. Major elements of attachment structure 306 include ingrowth plates 308 and 310 that each span a groove or trough 312 depressed below the curved outer surface 314 of the side of the femoral component 300. In this embodiment, trough 312 runs generally transverse to the longitudinal axis of the femur. Trough 312 is deep enough to accommodate the size of the suture needle to be used.

Each ingrowth plate 308 and 310 bows out convexly from the outer surface 314 of the femoral component 300, similarly to the ingrowth plates 204, 206 and 208 of the embodiment of FIG. 6 described above. The description above of ingrowth plates 204, 206 and 208 relative to the implant applies also to ingrowth plates 308 and 310 in this embodiment and is incorporated here. Such features and geometries for soft tissue attachment and ingrowth are applicable to various implants.

Figure 12:
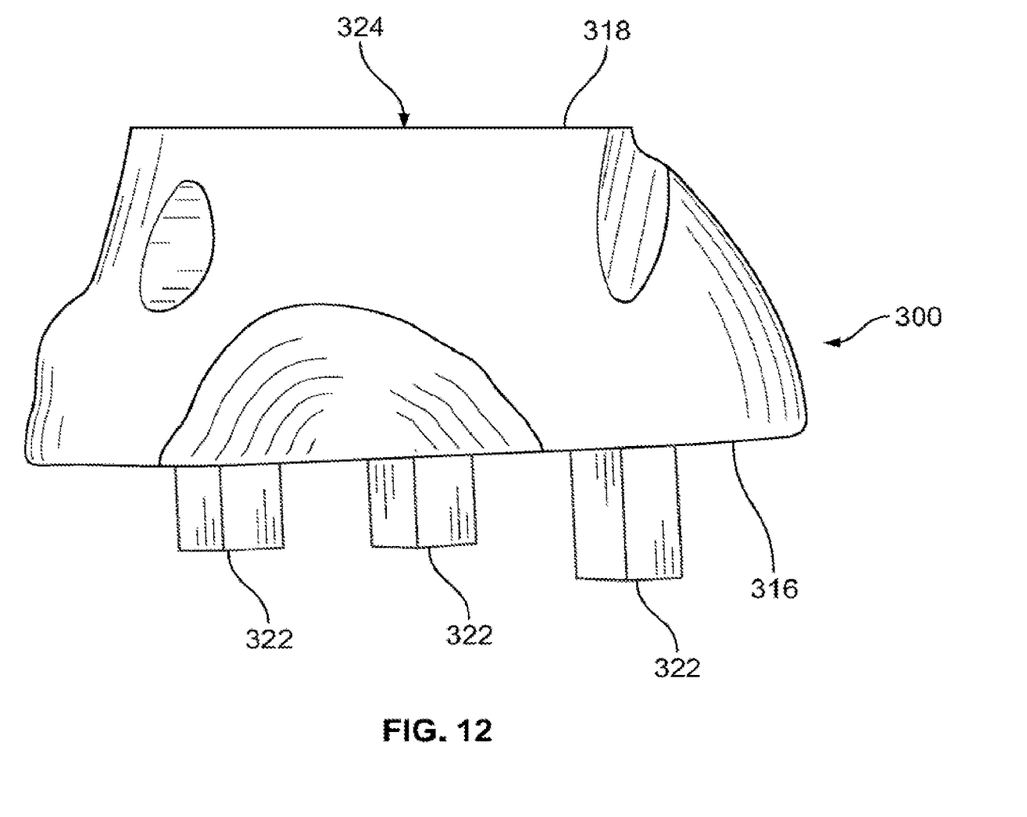
FIG. 12 is a front view of the femoral component of FIG. 11.
Figure 13:
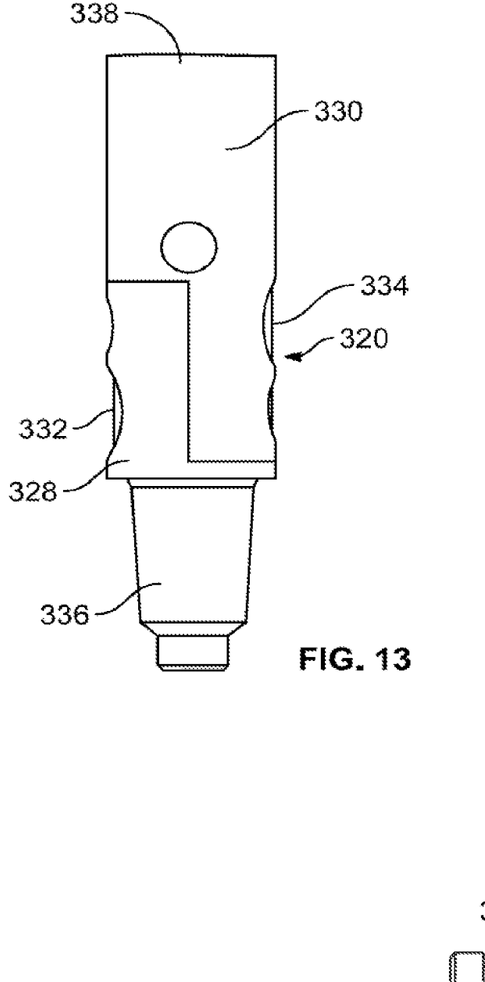
FIG. 13 is a front view of an assembled mid-section element of an orthopedic implant.
Figure 14:
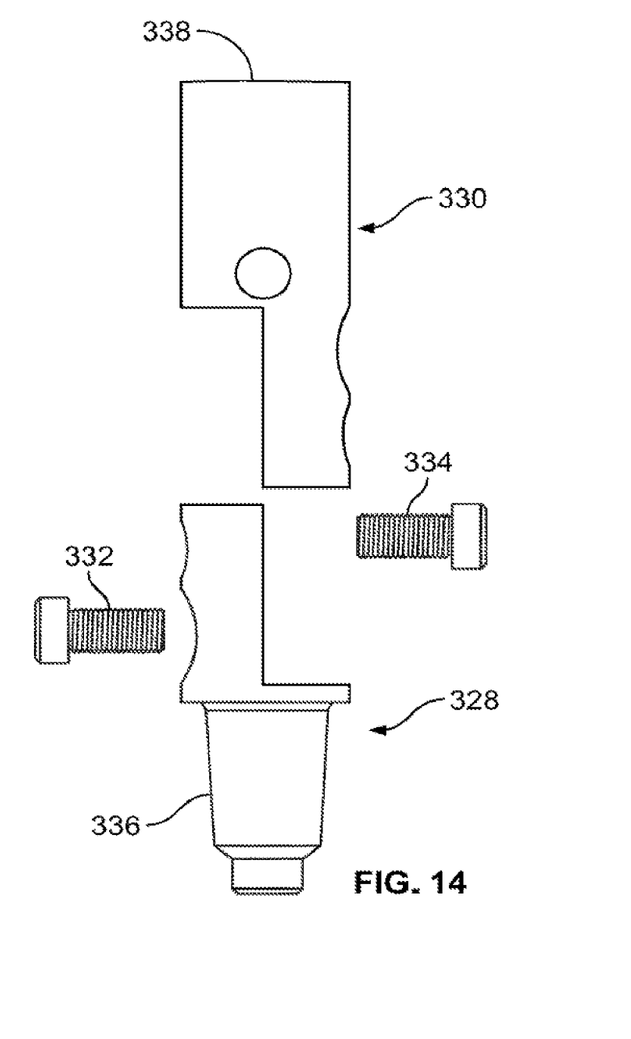
FIG. 14 is a front view of the disassembled mid-section element of FIG. 13.

FIG. 12 illustrates femoral segment component 300 which is generally shaped as a conical frustum corresponding in anatomical structure to the resected segment of the metaphyseal/epiphyseal bone that it replaces. The wider base surface 316 approximates the dimensions of the cut metaphyseal or epiphyseal bone. Certain dimensions of top surface 318 are configured to mate with those of a second, mid-section element 320 as illustrated in FIGS. 13 and 14. The curved outer surface 314 of component 300 is shaped to mimic the outer surface of the resected metaphyseal or epiphyseal bone in order to allow for ideal functioning of the nearby joint, for example to allow for smooth gliding of the patella.

Figure 16:
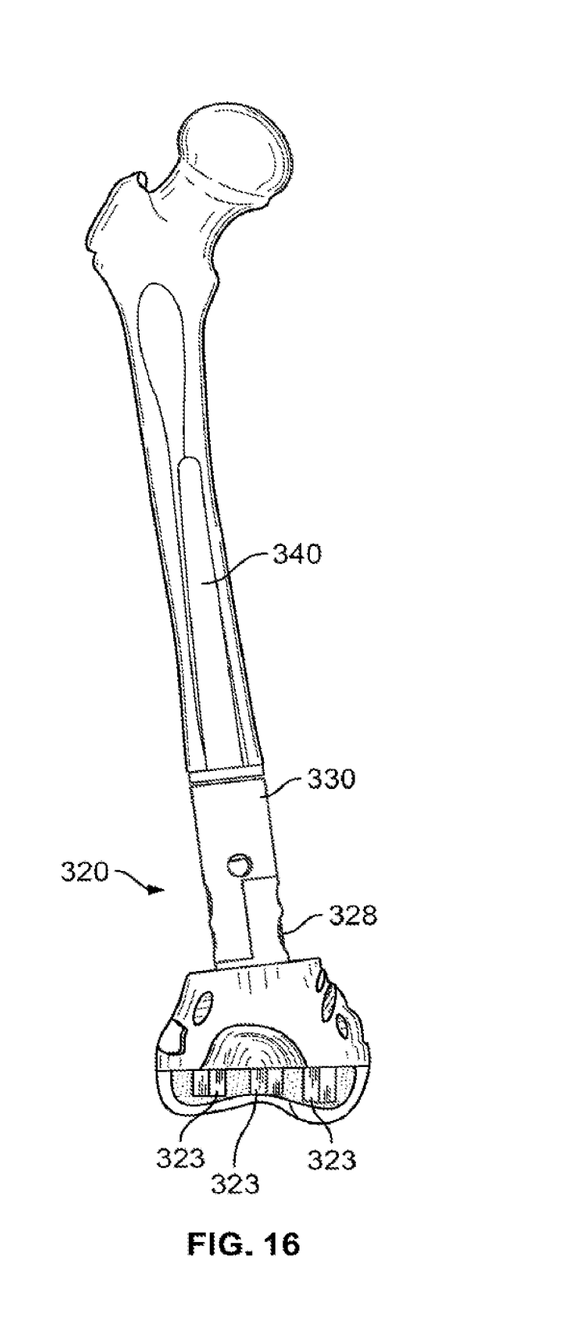
FIG. 16 is a front view of the elements of FIG. 15 fully assembled and implanted into bone.

The base 316 of component 300 comprises one or more contiguous planes corresponding to the plane(s) of bone resection. One or more pegs 322 with polygonal outer aspects, or other shapes, and having various lengths extend from the base 316 of component 300. The pegs 322 will be inserted into the remaining metaphyseal or epiphyseal bone (see FIG. 11). This polygonal outer aspect of the pegs 322 promotes an initial interference fit when inserted into corresponding, slightly narrower cylindrical holes 323 in the bone (see FIG. 16). Of course, other configurations of pegs and mating receiving holes are envisioned. All aspects of component 300 in contact with bone may have porous surfaces or other surface treatments for facilitating bone ingrowth.

Figure 15:
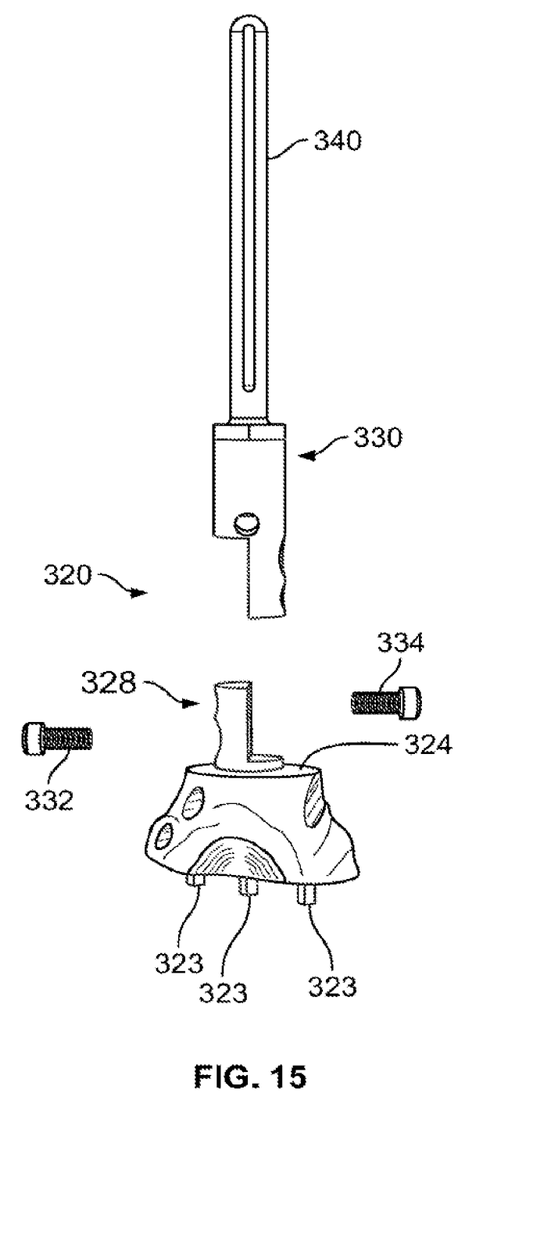
FIG. 15 is a front view of the femoral component of FIG. 12 connected to the disassembled mid-section element of FIG. 13, which is further connected to a diaphyseal stem.

Femoral component 300 includes a tapered cylindrical cavity 324 in its top surface 318 to make a secure, reversible connection with mid-section element 320, as shown in FIGS. 13 and 15. Of course, other interconnecting geometries are contemplated.

Mid-section element 320 comprises two elongated, partially overlapping elements 328 and 330 that are securely connected to each other at the time of surgery, or otherwise, using one or more bolts 332, 334 or other fastening devices. Element 328 includes a tapered cylindrical portion 336, also known as a Morse taper, that removably connects to the cylindrical cavity 324 of component 300. An upper end 338 of element 330, further from the knee joint, includes another well-known tapered cylindrical cavity (not shown) to make a secure connection with other prosthetic implants that connect to the remaining diaphyseal bone.

In FIG. 15, the upper element 330 of mid-section element 320 is shown connected to a typical diaphyseal stem 340 by way of a known Morse taper connection. Of course, other technologies for the connection, which technologies are well known to those skilled in the art, are contemplated. As further depicted in FIG. 15, the two-part mid-section 320 can be disassociated and removed without distraction of the entire assembly as would otherwise be required to disengage cylindrical connectors (e.g. Morse tapers). Distraction would be especially challenging for an implant that spares the natural joint surface due to the surrounding soft tissues. This mid-section can be exchanged later for a longer one to match a growing contralateral limb. Conversely, a midsection element which can elongate via a telescoping mechanism (not shown) can be utilized.

In order to meet the dimensional requirements discussed above, component 300 is preferably produced using additive manufacturing, also known as 3D printing. Additive manufacturing allows for complex metallic geometries to be produced that match a single or multi-plane bone resection.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Other embodiments of the invention will be apparent to those skilled in the art from consideration of the specification and practice of the invention disclosed herein. Although specific advantages have been enumerated above, various embodiments may include some, none, or all of the enumerated advantages. It is intended that the embodiments described above be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

In any interpretation of the claims appended hereto, it is noted that no claims or claim elements are intended to invoke or be interpreted under 35 U.S.C. 112(f) unless the words "means for" or "step for" are explicitly used in the particular claim.

The invention claimed is:

1. A method for affixing soft tissue to an implant, comprising the steps of:
   providing an implantable component having a soft tissue attachment structure including a surface defining a trough, and
   at least one ingrowth plate spanning the trough from a first end of the trough to a second end of the trough, the at least one ingrowth plate being a plate defining holes for tissue ingrowth, the at least one ingrowth plate defining a suture tunnel between the at least one ingrowth plate and trough for receiving a suture;
   implanting the implantable component to skeletal bone such that soft tissue overlies the at least one ingrowth plate; and
   passing the suture through the trough from the first end, over the soft tissue overlying the at least one ingrowth plate, to the second end, and back through the trough in a loop.

2. The method of claim 1, wherein the at least one ingrowth plate bows convexly away from the surface.

3. The method of claim 1, wherein the at least one ingrowth plate has a first reinforcing rod having a first outer surface with first and second depressions therein, the method further comprising the steps of placing and stabilizing the suture within the first and second depressions, and overlying and compressing soft tissue against the ingrowth plate, whereby soft tissue ingrowth and fixation is facilitated.

4. The method of claim 3, wherein the at least one ingrowth plate further includes a second reinforcing rod having a second outer surface with third and fourth depressions therein, the method further comprising the steps of placing and stabilizing the suture within the third and fourth depressions, and overlying and compressing soft tissue against the ingrowth plate, whereby soft tissue ingrowth and fixation is facilitated.

5. The method of claim 4, wherein the first and second reinforcing rods are integral with the at least one ingrowth plate and span a portion of the trough.

6. A method for affixing soft tissue to an implant, comprising the steps of:
   providing an implantable component having a soft tissue attachment structure including a surface defining a trough, and an ingrowth plate spanning a portion of the trough from a first end of the trough to a second end of the trough, and defining a suture tunnel between the ingrowth plate and trough for receiving suture, the ingrowth plate being a plate defining holes for tissue ingrowth, wherein the ingrowth plate bows convexly away from the surface;
   implanting the implantable component to skeletal bone such that soft tissue overlies the convex ingrowth plate; and
   passing suture through the trough from the first end, over the soft tissue overlying the ingrowth plate, to the second end, and back through the trough in a loop.

7. A method for affixing soft tissue to an implant, comprising the steps of:
   providing an implantable component having a soft tissue attachment structure including a surface defining a spaced pair of troughs;

a first fixation bridge spanning a portion of one of the pair of troughs; and a second fixation bridge spanning a portion of the other of the pair of troughs, the second fixation bridge being separated from the first fixation bridge;

each fixation bridge and respective trough defining a suture tunnel for receiving suture;

wherein the surface further defines a soft tissue ingrowth patch between the spaced pair of troughs, the ingrowth patch being a plate defining holes for tissue ingrowth;

implanting the implantable component to skeletal bone such that soft tissue overlies the soft tissue ingrowth patch; and passing a suture through a first one of the spaced pair of troughs, from a first end of the first one of the spaced pair of troughs, over the soft tissue overlying the soft tissue ingrowth patch, to a second end of the first one of the spaced pair of troughs, and back through the first one of the spaced pair of troughs in a loop.

8. The method of claim 7, further comprising the step of passing a suture through a second one of the spaced pair of troughs, over the soft tissue overlying the soft tissue ingrowth patch, and back through the second one of the spaced pair of troughs in a loop.

9. The method of claim 7, wherein the soft tissue ingrowth patch includes a porous structure having pore spacing that is receptive to soft tissue, the method further comprising pressing the soft tissue overlying the soft tissue ingrowth patch into contact with the porous structure to promote growth thereto and fixation of the soft tissue to the implantable component.

10. The method of claim 9, further comprising the step of accommodating multiple sutures under one of the first fixation bridge and the second fixation bridge, whereby more pressure may be applied to the soft tissue to facilitate more ingrowth of tissue.

\* \* \* \* \*